United States Patent [19]
Grossi et al.

[11] Patent Number: 4,955,884
[45] Date of Patent: Sep. 11, 1990

[54] SYSTEM FOR REDUCING DRAG ON THE MOVEMENT OF AN ELECTRODE IN A RESECTOSCOPE

[75] Inventors: Benedetto Grossi; Raymond Ainger, III, both of Stamford, Conn.; Richard P. Muller, Bronx, N.Y.

[73] Assignee: Circon Corporation, Santa Barbara, Calif.

[21] Appl. No.: 201,667

[22] Filed: Jun. 2, 1988

[51] Int. Cl.$^5$ .............................................. A61B 17/36
[52] U.S. Cl. ....................................................... 606/46
[58] Field of Search ........... 128/303.1, 303.13, 303.17; 606/41, 45, 46, 49

[56] References Cited

U.S. PATENT DOCUMENTS

| | | | |
|---|---|---|---|
| D. 251,608 | 4/1979 | Cawood, Jr. et al. | D24/18 |
| D. 251,609 | 4/1979 | Cawood, Jr. et al. | D24/18 |
| 2,008,526 | 7/1935 | Wappler et al. | 128/303.15 |
| 3,835,842 | 9/1974 | Iglesias | 128/303.15 |
| 3,850,162 | 11/1974 | Iglesias | 128/6 |
| 4,132,227 | 1/1979 | Ibe | 128/4 |
| 4,149,538 | 4/1979 | Mrava et al. | 128/303.15 |
| 4,325,374 | 4/1982 | Komiya | 128/303.15 |
| 4,538,610 | 9/1985 | Kubota | 128/303.15 |
| 4,726,370 | 2/1988 | Karasawa et al. | 128/303.15 |

FOREIGN PATENT DOCUMENTS

| | | |
|---|---|---|
| 2528543 | 1/1976 | Fed. Rep. of Germany ........................ 128/303.14 |
| 2449559 | 4/1976 | Fed. Rep. of Germany ........................ 128/303.15 |
| 2915271 | 10/1980 | Fed. Rep. of Germany ........................ 128/303.15 |

OTHER PUBLICATIONS

The New Continuous Flow Resectoscope From American ACMI, May 1984.
"ACMI Continuous Flow Resectoscope" Jan. 1987.
"Operating and Maintenance Manual Continuous Flow Resectoscope" American ACMI, Apr. 1983.
"ACMI Adult Resectoscope Operating & Maintenance Manual", American ACMI, Jun. 1984.

Primary Examiner—Max Hindenburg
Attorney, Agent, or Firm—Perman & Green

[57] ABSTRACT

A system for reducing drag in a resectoscope working element. A hole is provided at a proximal end of a substantially enclosed electrode sheath for exiting fluids and substantially preventing pressure from being generated in the sheath. A working element has a guide block with a guide bar channel having a first cross-sectional shape and a guide bar with a second cross-sectional shape such that there are spaces between the guide bar and the guide bar channel and the bearing surfaces therebetween are relatively small.

18 Claims, 1 Drawing Sheet

SYSTEM FOR REDUCING DRAG ON THE MOVEMENT OF AN ELECTRODE IN A RESECTOSCOPE

BACKGROUND OF THE INVENTION

1. Field of the Invention

This invention relates to medical endoscopes and, more particularly, to a system for reducing drag on the movement of an electrode in a resectoscope and a method of making the same.

2. Prior Art

A typical resectoscope for transurethral resection consists of four main elements. The first element is a rigid endoscope or telescope for observing the interior of the human bladder, or operative sites near the base of the urethra. The endoscope comprises an objective lens and a series of relay lenses housed within an endoscope barrel or stem, the stem being connected to an eyepiece housing containing suitable lenses for proper magnification. The second element takes the form of a handle assembly commonly referred to as a working element. The working element serves as the means for connecting electrosurgical current from an electrosurgical generator to the third element, an electrode assembly. The working element is also capable of slidably moving the electrode assembly axially, such axial movement being observable through the eyepiece of the endoscope. The combination of the endoscope, working element, and electrode assembly is locked into a fourth element, a resectoscope sheath. The sheath consists of a tube and a union body and lock assembly. In an operative procedure the sheath is placed into the urethra prior to introduction of the other elements.

The electrode assembly is removably connected to a guide block of the working element. The guide block is movable such as by a rack and pinion mechanism or by an operator deflecting a spring to advance or retract the electrode assembly. The guide blocks in the prior art generally are mounted on one or more guide bars of the working element. The guide bars have been known to be either circular or square in cross-section with guide bar apertures in the guide block also being matingly circular or square in cross-sectional shape, respectively. The guide block is thus slidingly mounted on the guide bar or bars. Lubrication is generally provided by the guide block by having the block comprised of Teflon, a trademark of E.I. Dupont Co., or a similar material. Prior art resectoscope working elements, in addition to a telescope sheath, generally also have an electrode assembly sheath. The electrode assembly is generally slidably connected to either the telescope and/or an electrode guide of the working element. The electrode sheaths have generally been known to be of two types; a substantially enclosed tube or a partial tube with a longitudinal slot along its entire length. The longitudinally slotted electrode sheaths, however, can only use an electrode assembly with a rigid outer sleeve along substantially its entire lead because of the lack of rigidity in the slotted electrode sheath. The substantially enclosed tube electrode sheaths provide sufficient rigidity such that electrode assemblies without rigid outer sleeves or with flexible leads can be used therein.

However, problems have arisen in the devices known in the prior art. First, it is desirable to use electrode assemblies that do not have rigid outer sleeves or do not have sleeves along their entire lead because they allow for greater design options in the means of bringing electrosurgical power from a power cord to the electrode at its proximal end. However, the use of an electrode assembly having a flexible lead requires the use of a working element having an electrode sheath with a substantially enclosed tube. Because fluids and other materials can enter the electrode sheath at its open distal end and, because the proximal end is sealed to prevent leakage external of the resectoscope, fluid between the electrode sheath and the electrode assembly can cause drag or hinder the movement of the electrode assembly because of such factors as fluid friction and the incompressability of fluids in the electrode sheath; the proximal end of the electrode sheath being substantially sealed.

Another problem arises in the devices known in the prior art in that the movement of the guide block on the guide bar of the working element, and thus the movement of the electrode assembly, can be hindered by accumulations of fluids or debris on the guide bar.

Fluid from a resectoscope operation can exit the resectoscope, especially when the working element is removed to use an evacuator, and lodge on the guide bars which can at least partially dry and form a sticky barrier to the smooth movement of the guide block on the guide bar. Because of the delicacy involved with resectoscope operations it is desirous to provide a smooth sliding guide block. Dried fluids or debris that come between the guide block and guide bar can cause drag or hinder this smooth movement.

It is therefore an objective of the present invention to provide a working element with an electrode sheath that can support an electrode assembly with a flexible lead and also allow fluids to exit the sheath and thereby substantially prevent fluid friction or pressure caused by movement of the electrode assembly relative to the electrode sheath from hindering the movement of the electrode assembly.

It is another objective of the present invention to provide a working element with a guide block that will not have its smooth movement substantially hindered because of liquids or deposits on the guide bar or between the guide bar and guide block.

SUMMARY OF THE INVENTION

The foregoing problems are overcome and other advantages are provided by a system for reducing drag on the movement of an electrode in a resectoscope working element.

In accordance with one embodiment of the invention, a system is provided comprising electrode sheath means; means for sealing the sheath means proximate a proximal end; and means for exiting fluids from the electrode sheath. The sheath comprises a tube substantially enclosed and has an open distal end and a proximal end for movement of the electrode therein.

In accordance with another embodiment of the invention, a resectoscope is provided comprising guide block means and means for providing a relatively smooth and precise slide of the guide block means on at least one guide bar. The guide block means is slidably mounted on the guide bar and has a guide bar channel with a first cross-sectional shape. The guide bar has a second cross-sectional shape.

In accordance with one method of the invention, a method of manufacturing a resectoscope is provided comprising the steps of providing a guide bar of the resectoscope with a first cross-sectional shape; and mounting a guide block onto the guide bar. The guide bar channel has a second cross-sectional shape with the guide bar channel making a slidable fit therewith and having predetermined spaces therebetween whereby a relatively small amount of bearing area is provided between the bar and the channel.

BRIEF DESCRIPTION OF THE DRAWINGS

The foregoing aspects and other features of the invention are explained in the following description, taken in connection with the accompanying drawings wherein.

DETAILED DESCRIPTION OF THE INVENTION

Figure 1:
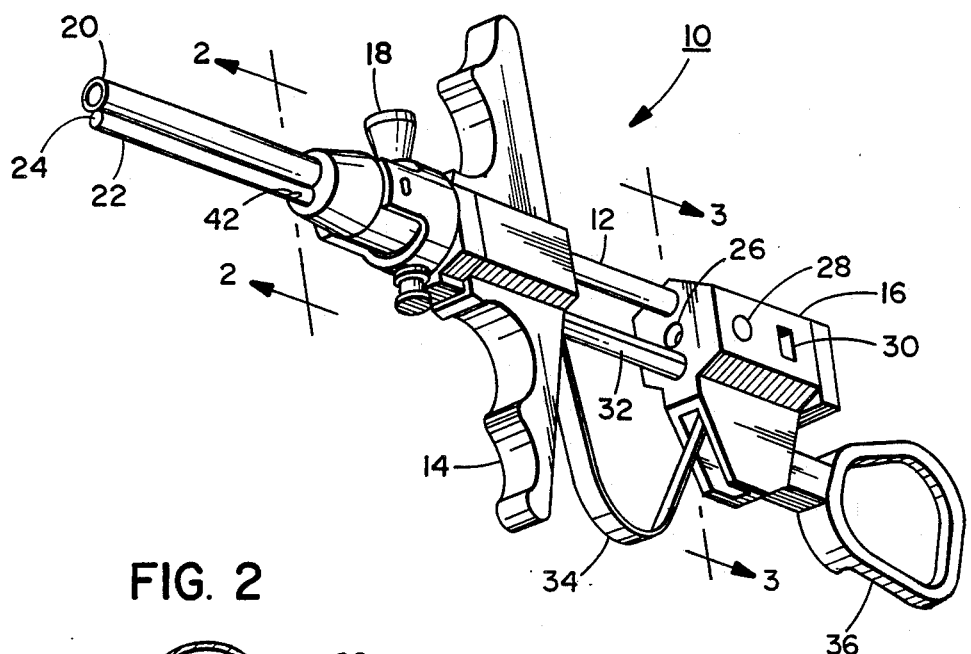
FIG. 1 is a perspective view of a resectoscope working element incorporating features of the invention.

Referring to FIG. 1, there is shown one embodiment of a resectoscope working element 10 incorporating features of the invention. Although the present invention will be described with reference to resectoscopes, it should be understood that the present invention can be used with any suitable type of endoscope. In addition, any suitable size, shape or type of material can be used in the elements of the present invention. Cross reference is hereby made to the following copending patent applications; "System For Disconnectably Mounting An Endoscope Sheath With An Endoscope Tool", Ser. No. 07/202,152, filed June 2, 1988; "Improved Resectoscope Electrode and Method For Making The Same" by Grossi et al., Ser. No. 07/202,153, filed June 2, 1988; Grossi et al, Ser. No. 07/202,154, filed June 2, 1988; Design For A "Resectoscope Electrode", by Grossi et al, Ser. No. 07/203,021, filed June 2, 1988; and Design For A "Resectoscope Sheath Latch Receptacle" by O'Hare et al., Ser. No. 07/201,711, filed June 2, 1988 and Design for a "Resectoscope Electrode" Ser. No. 07/203,022, filed June 2, 1988 assigned to the same assignee as herein and which are incorporated by reference in their entirety herein.

The working element 10, in this embodiment, generally comprises a frame 12, a handle 14, a movable guide block 16, a connecting cone and movable latch assembly 18, a telescope sheath 20 and an electrode assembly sheath 22. The telescope sheath 20 and electrode assembly sheath 22 are generally intended for insertion into a resectoscope sheath (not shown) with the cone and movable latch assembly 18 making a sealable, but disconnectable connection therewith. A telescope (not shown) is generally positioned in the telescope sheath 20. An electrode assembly (not shown) is generally positioned, at least partially, in the electrode assembly sheath 22 with a distal end of the electrode assembly extending from an open distal end 24 of the sheath 22. A proximal end of the electrode assembly extends through the cone and latch assembly 18, handle 14 and into an aperture 26 in the guide block 16. The proximal end of the electrode assembly is fixedly but disconnectably attached to the guide block 16 by a connecting means 28. An electrical plug (not shown) is inserted into a socket 30 in the guide block 16 and makes an electrical contact with the proximal end of the electrode assembly such that electrosurgical current can be supplied to the electrode assembly for performing a desired operation. The electrode assembly is generally connected to the distal end of the telescope and slidably movable relative thereto along an axially relative path. The guide block 16 is provided such that the operator can move the electrode assembly along its axial path. The guide block 16 is slidably mounted, in this embodiment, on a portion of the telescope sheath 20 and a guide bar 32 of the frame 12. A spring 34 is provided between the guide block 16 and handle 14 such that the guide block 16 and electrode assembly are generally retained in a first position. An operator, with the thumb of one hand in a thumb guide 36 and other fingers of the same hand on the handle 14, can move the guide block 16 towards the handle 14 along the guide bar 32 and telescope sheath 20. With the movement of the guide block 16, the spring 34 is deflected and the electrode assembly is generally advanced through the electrode assembly sheath 22. When the operator desires to retract the electrode assembly, he reduces the force exerted between the thumb guide 36 and handle 14 whereby the spring 34 will move the guide block 16 back towards its first position axially moving the electrode assembly therewith.

Figure 2:
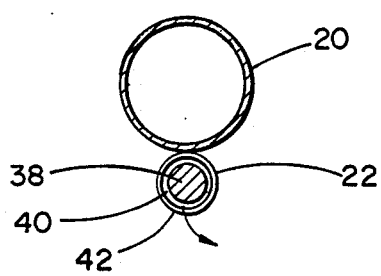
FIG. 2 is a cross-sectional view of the working element of FIG. 1 taken along lines 2—2.

Referring also to FIG. 2, there is shown a cross sectional view of the telescope sheath 20 and electrode assembly sheath 22 of the working element 10 in FIG. 1 taken across line 2—2. In this view, the electrode assembly 38 is shown in the electrode assembly sheath 22. As described above, the electrode assembly 38 generally moves in the electrode assembly sheath 22 along a reciprocating axial path. The electrode assembly 38 is slightly smaller than the inner diameter of the electrode assembly sheath 22 such that a space 40 is provided between the assembly 38 and sheath 22. In this embodiment, located at the proximal end of the electrode assembly sheath 22 is a bleed hole 42. A suitable seal (not shown) is provided in the cone and latch assembly 18 such that the electrode assembly sheath 22 is substantially sealed at its proximal end when the electrode assembly 38 is positioned therein.

The electrode assembly sheath 22 is generally tube shaped and relatively rigid and enclosed. The electrode assembly 38 has a lead portion which, because the electrode assembly is desired to be disposable, is manufactured in a relatively inexpensive manner without a rigid outer sheath, the lead section is substantially flexible. Thus the electrode assembly sheath 22 is substantially enclosed and provides rigidity along its entire length to provide a fixed and definite path for the electrode assembly 38 such that the assembly 38 which includes a shaft which will not buckle or bend while being pushed by the guide block 16. Because the relatively small space 40 is provided between the electrode assembly sheath 22 and the electrode assembly 38 for relative movement therebetween, fluids such as irrigants can enter the open distal end 24 between the electrode assembly sheath 22 and the electrode assembly 38. The bleed hole 42 is provided at the proximal end of the electrode assembly sheath 22 such that when the electrode assembly 38 reciprocates back and forth along its axial path in the electrode assembly sheath 22 the bleed hole 42 can cooperate with the open distal end 24 such that the fluid between the sheath 22 and the electrode assembly 38 will not substantially hinder that movement. When the guide block 16 and electrode assembly 38 are in a retracted home position and an operator advances the guide block and thus advances the electrode assembly 38 the surface of the electrode assembly 38 frictionally draws at least a portion of the liquid in the space 40 with it as it advances forward. The bleed hole 42 substantially prevents a vacuum from being created in the space 40 because of the movement of the liquid. Oppositely, when the electrode assembly 38 is in a fully extended position and the operator allows the guide block 16 to retract back to the home position the electrode assembly 38 moves rearwardly in the electrode assembly sheath 22. The bleed hole 42 allows fluid being moved by the frictional attraction of the surface of the electrode assembly 38 to be exited from the sheath 22, thereby substantially preventing fluid pressure build-up created by the moving fluid in the sheath 22 from hindering the movement of the electrode assembly 38. Alternatively, two or more bleed holes may be provided.

Figure 3:
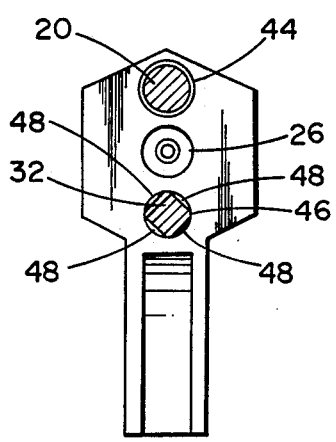
FIG. 3 is a cross-sectional view of the working element of FIG. 1 taken along lines 3—3.

Referring now to FIG. 3, there is shown a front end view of the guide block 16 shown in FIG. 1 taken along lines 3—3. The guide block in this embodiment is generally comprised of a suitable material such as Teflon, a Trademark of E.I. Dupont Co. In addition to the electrode assembly proximal end aperture 26, connecting means 28 and socket 30, the guide block 16 comprises a telescope sheath aperture 44 and a guide bar aperture 46. The guide block 16 is slidably mounted on the proximal end of the telescope sheath 20 and the guide bar 32 with the telescope sheath 20 passing through the telescope sheath aperture 44 and the guide bar 32 passing through the guide bar aperture 46. In this embodiment, both the telescope sheath aperture 44 and guide bar aperture 46 are provided with a generally circular cross section. The proximal end of the telescope sheath 20, in this embodiment, also has a generally circular cross section that slidably fits within the telescope sheath aperture 44 and also acts as a torque stabilizer for the guide block 16. However, in this embodiment, the guide bar 32 has a generally square cross section, but which nonetheless is suitably sized such that it can be snugly and slidably mounted in the guide bar aperture 46. In this embodiment, the distance between opposite corners or the diagonal is substantially equivalent or slightly less than the diameter of the narrowest portion of the guide bar aperture 46. The corners of the guide bar 32 provide a relatively small bearing area or surface or substantially reduced contact area than might otherwise be considered necessary between the guide bar 32 and the guide bar aperture 46. In addition, spaces 48 are provided on each side of the guide bar 32 between the guide bar and the guide bar aperture 46. The spaces 48 provide flushing areas between the guide block 16 and guide bar 32 for cleaning or the like.

One of the principle features of the present invention is that the spaces 48 between the guide bar 32 and the guide bar aperture 46, along with the relatively small bearing area between the guide bar and the guide bar aperture, allow the guide block 16 to slidingly move along the guide bar 32 with a greatly diminished risk that accumulations of fluids or the like on the guide bar 32 will hinder the movement of the guide block 16. The spaces 48 provide an area where material can pass between the guide bar 32 and the guide bar aperture 46 without hindering the movement of the guide block 16. The relatively small bearing area between the guide bar 32 and guide bar aperture 46 allows a greater force to be applied to any accumulations on the corners of the guide bar 32 or on the guide bar aperture 46 without increasing the strength of the spring 34 or the operator having to apply additional force. Any accumulations about the corners of the guide bar 32 can be relatively easily pushed away from the bearing surface and into the spaces 48.

Figure 4:
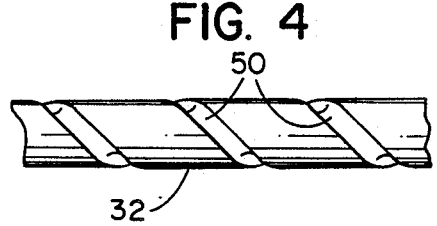
FIG. 4 is a partial side view of a guide bar of an alternate embodiment of the invention.
Figure 5:
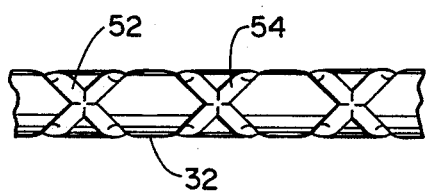
FIG. 5 is a partial side view of a guide bar of an alternate embodiment of the invention.

In an alternate embodiment the guide bar aperture 46 may be provided with a square cross section and the guide bar 32 may be provided with a circular cross section. Alternatively, any suitable different cross sectional shapes may be provided for the guide bar 32 and guide bar aperture 46. In addition, the proximal end of the telescope sheath 20 and the telescope sheath aperture 44 may also be provided with different cross sectional shapes. Referring now to FIGS. 4 and 5, alternate embodiments of the present invention are shown. In the embodiment in FIG. 4, a partial side view of a guide bar 32 is shown. In this embodiment, the guide bar 32 generally comprises a circular type cross section intended for use with a circular type cross sectional guide bar aperture of a guide block. However, in this embodiment, the guide bar 32 comprises a helical groove 50 about its outer perimeter. The helical groove 50 provides a space between the guide bar 32 and the cooperating guide block. This space, similar to the spaces 48 in the embodiment shown in FIGS. 1 and 3, provides a place where material on the surface of the guide bar 32 can be quickly and easily removed from the bearing surface of the guide bar. In addition, the helical nature of the groove 50 combines with the movement of the guide block 16 to act as a type of auger to substantially remove any material that might otherwise accumulate in the interior of the guide bar aperture. FIG. 5, also shows a partial side view of a guide bar 32 of an alternate embodiment of the invention wherein the guide bar 32 generally comprises two helical grooves 52, 54 on the guide bar having opposite directions of wrap. In this embodiment, the grooves 52, 54 perform a similar function as the groove 50 described with reference to FIG. 4. However, in this embodiment, the auger or cleaning nature of the grooves 52, 54 is substantially greater than the single groove construction shown in FIG. 4. In an alternate embodiment of the invention the guide bar aperture of the guide block may alternatively or additionally comprise grooves therein. In another alternate embodiment, a cross sectionally square guide bar may be provided with spaced helical type grooves on its corners. As is evident from the above description any suitable different combination of cross sectional shapes can be provided by providing grooves in the guide bar and/or the guide bar aperture of the guide block to provide a relatively smooth and precise slide of the guide block on the guide bar.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A system for reducing resistance on the movement of an electrode having a distal end and a shaft in a resectoscope working element, the system comprising:
   electrode sheath means comprising a substantially enclosed tube having an open distal end and a proximal end for axial movement of the electrode therein, said distal end having a dimension which permits the electrode to be passed therethrough;

means for substantially sealing said sheath means proximate said proximal end; and means positioned adjacent the path defined by axial movement of the shaft of the electrode for exiting fluids during axial movement of the shaft of the electrode thereacross, other than at said open distal end, from said electrode sheath.

2. A system as in claim 1 wherein said exiting means comprises at least one hole at a proximal region of said electrode sheath.

3. A system as in claim 1 wherein said exiting means comprises at least two holes in said electrode sheath.

4. A system as in claim 2 wherein a relatively small space is provided between the electrode sheath means and the electrode enabling said hole and said open distal end cooperate to substantially prevent fluid in said electrode sheath from hindering the movement of an electrode in said sheath.

5. A system as in claim 1 wherein a relatively small space is provided between the electrode sheath means and the electrode enabling said means for exiting fluids to also function s a means for preventing pressure from being generated in said electrode sheath.

6. A resectoscope working element having means for moving an extendable electrode, the working element comprising:

guide block means for moving the electrode relative to a telescope, said guide block means being slidably mounted on at least one guide bar means; and means for providing a relatively smooth and precise movement of said guide block means on said at least one guide bar means, said movement means comprising said guide block means having a guide bar channel with a first cross-sectional shape and said at least one guide bar means having a second cross-sectional shape.

7. A working element as in claim 6 wherein said guide block means and said guide bar means have a relatively small bearing area therebetween.

8. A working element as in claim 6 wherein said guide block means and said guide bar means have spaces therebetween.

9. A working element as in claim 6 wherein said first cross-sectional shape is relatively circular.

10. A working element as in claim 6 wherein said second cross-sectional shape is relatively square.

11. A working element as in claim 6 wherein said guide bar means fits snugly into said guide bar channel.

12. A working element as in claim 9 wherein said second cross-section shape is relatively square with a distance between opposite diagonal corners being slightly smaller then the diameter of said first cross-sectional shape.

13. A working element as in claim 9 wherein said guide block means is comprised of Teflon.

14. A working element as in claim 9 wherein said at least one guide bar means has a groove means therein for providing a space between said guide block means and said at least one guide bar.

15. A working element as in claim 14 wherein said first cross-sectional shape is relatively circular and said second cross-sectional shape is generally circular with said groove means comprising at least one helical groove.

16. A working element as in claim 6 wherein said guide bar channel comprises a groove means therein.

17. A system for reducing resistance on the movement of an electrode in a resectoscope working element, the system comprising:

electrode sheath means comprising a substantially enclosed tube having an open distal end and a proximal end for movement of the electrode therein;

means for substantially sealing said sheath means proximate said proximal end;

means for exiting fluids, other than at said open distal end, from said electrode sheath; and means for providing relative movement between a guide block and a guide bar of the resectoscope, said movement means comprising said guide block having a guide bar channel with a first cross-sectional shape and said guide bar having a second cross-sectional shape whereby the movement of said guide block means on said guide bar is relatively smooth and precise.

18. A system as in claim 17 wherein said first cross-sectional shape is relatively circular and said second cross-sectional shape is relatively square.

* * * * *